(12) United States Patent
Shadduck

(10) Patent No.: US 6,911,028 B2
(45) Date of Patent: *Jun. 28, 2005

(54) MEDICAL INSTRUMENT WORKING END AND METHOD FOR ENDOLUMINAL TREATMENTS

(76) Inventor: John H. Shadduck, 1490 Vistazo West, Tiburon, CA (US) 94920

( * ) Notice: Subject to any disclaimer, the term of this patent is extended or adjusted under 35 U.S.C. 154(b) by 164 days.

This patent is subject to a terminal disclaimer.

(21) Appl. No.: 10/346,877

(22) Filed: Jan. 18, 2003

(65) Prior Publication Data

US 2003/0109869 A1 Jun. 12, 2003

Related U.S. Application Data

(63) Continuation-in-part of application No. 09/782,649, filed on Feb. 12, 2001, now Pat. No. 6,508,816, which is a continuation-in-part of application No. 09/181,906, filed on Oct. 28, 1998, now Pat. No. 6,210,404.

(51) Int. Cl.[7] .............................................. A61B 18/18
(52) U.S. Cl. ............................ 606/41; 606/46; 607/104
(58) Field of Search ........................ 606/38–41, 45–50; 607/101–105

(56) References Cited

U.S. PATENT DOCUMENTS

| | | | | |
|---|---|---|---|---|
| 4,682,596 A | * | 7/1987 | Bales et al. | 606/39 |
| 5,122,138 A | * | 6/1992 | Manwaring | 606/46 |
| 5,697,281 A | * | 12/1997 | Eggers et al. | 604/114 |
| 6,168,594 B1 | * | 1/2001 | LaFontaine et al. | 606/41 |
| 6,210,404 B1 | * | 4/2001 | Shadduck | 606/34 |
| 6,508,816 B2 | * | 1/2003 | Shadduck | 606/34 |

* cited by examiner

Primary Examiner—Michael Peffley
(74) Attorney, Agent, or Firm—Townsend and Townsend and Crew LLP

(57) ABSTRACT

A medical instrument that utilizes electrical energy delivery between first and second opposing polarity electrodes in an interior bore of a working end to cause vaporization of an inflowing fluid media. The vaporization and expansion of the fluid media creates pressure gradients in the working end that causes heated vapor to propagate distally from the working end. The propagation or jetting of the vapor media is used to controllably cause thermal effects in endoluminal environments. The instrument and method can be used to shrink and occlude blood vessels in a treatment for varicose veins.

20 Claims, 14 Drawing Sheets

AT TIME = $T_{ZERO}$

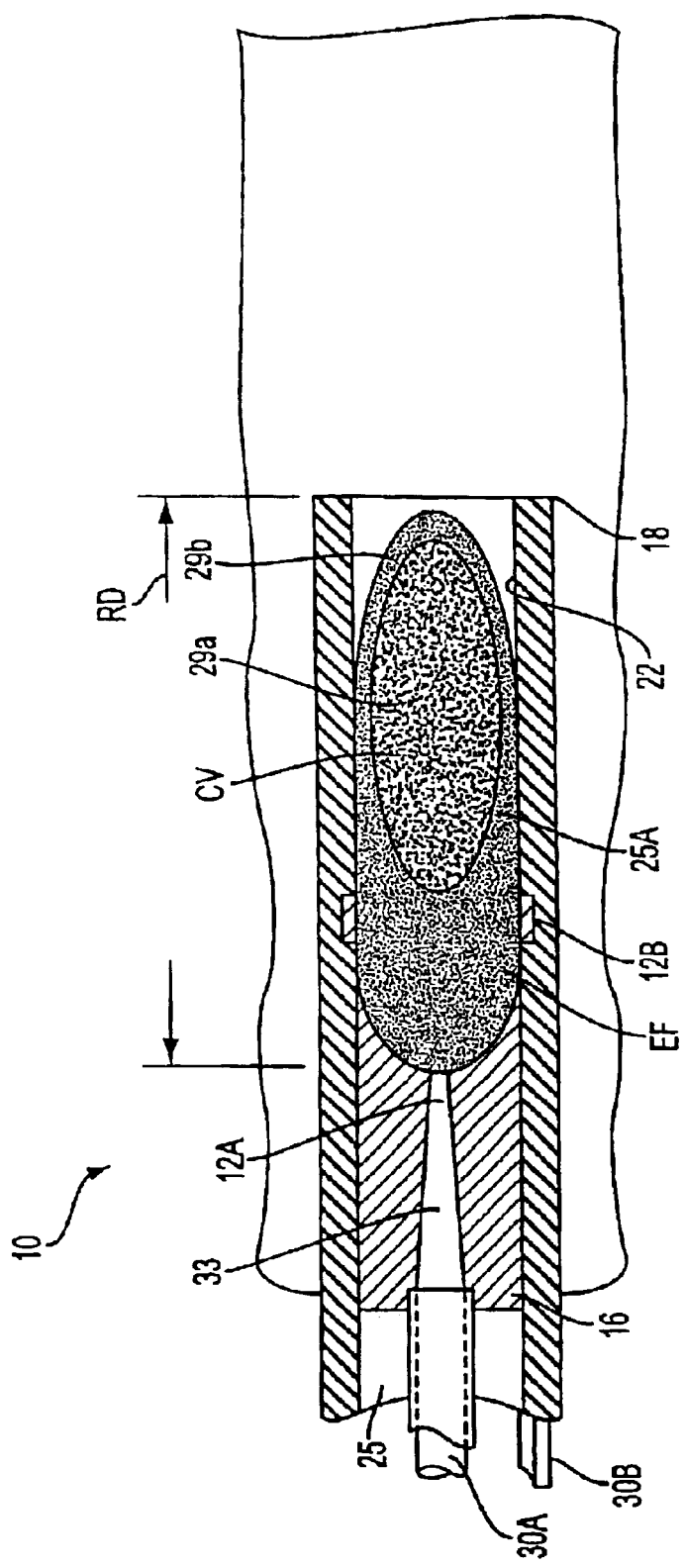

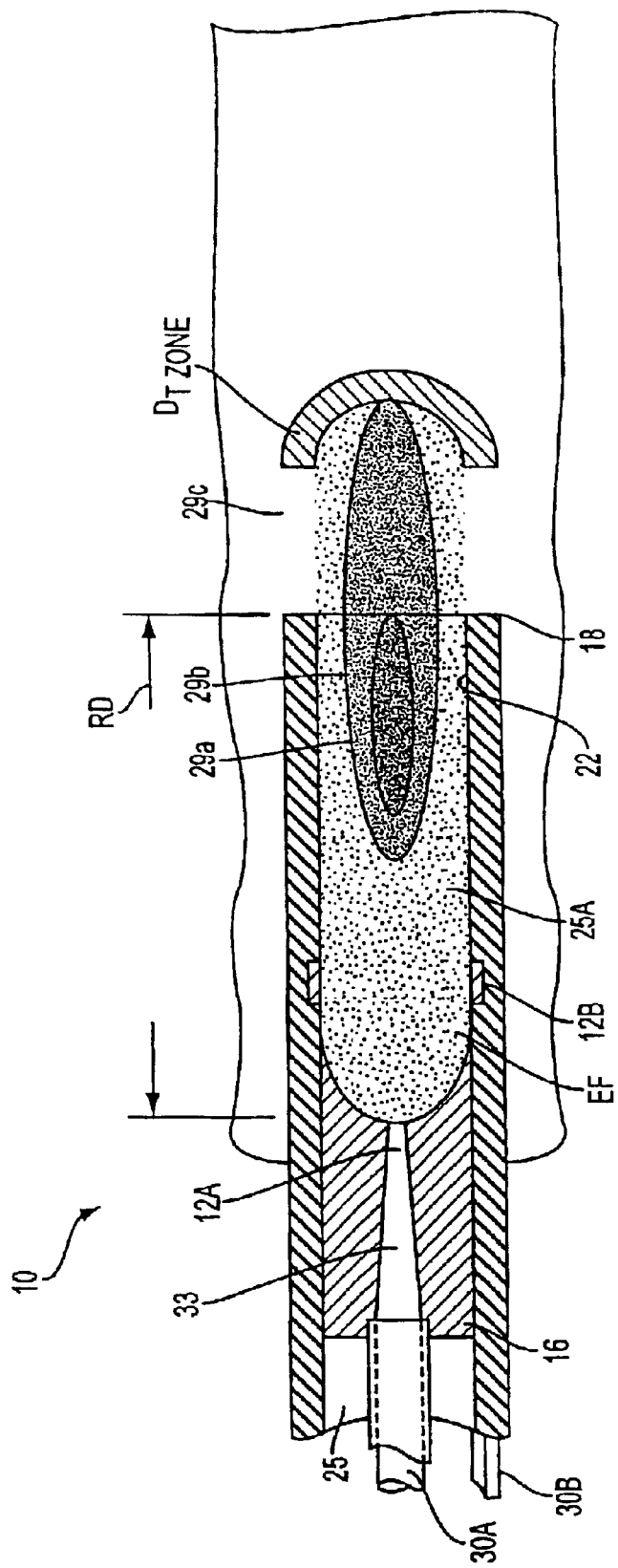

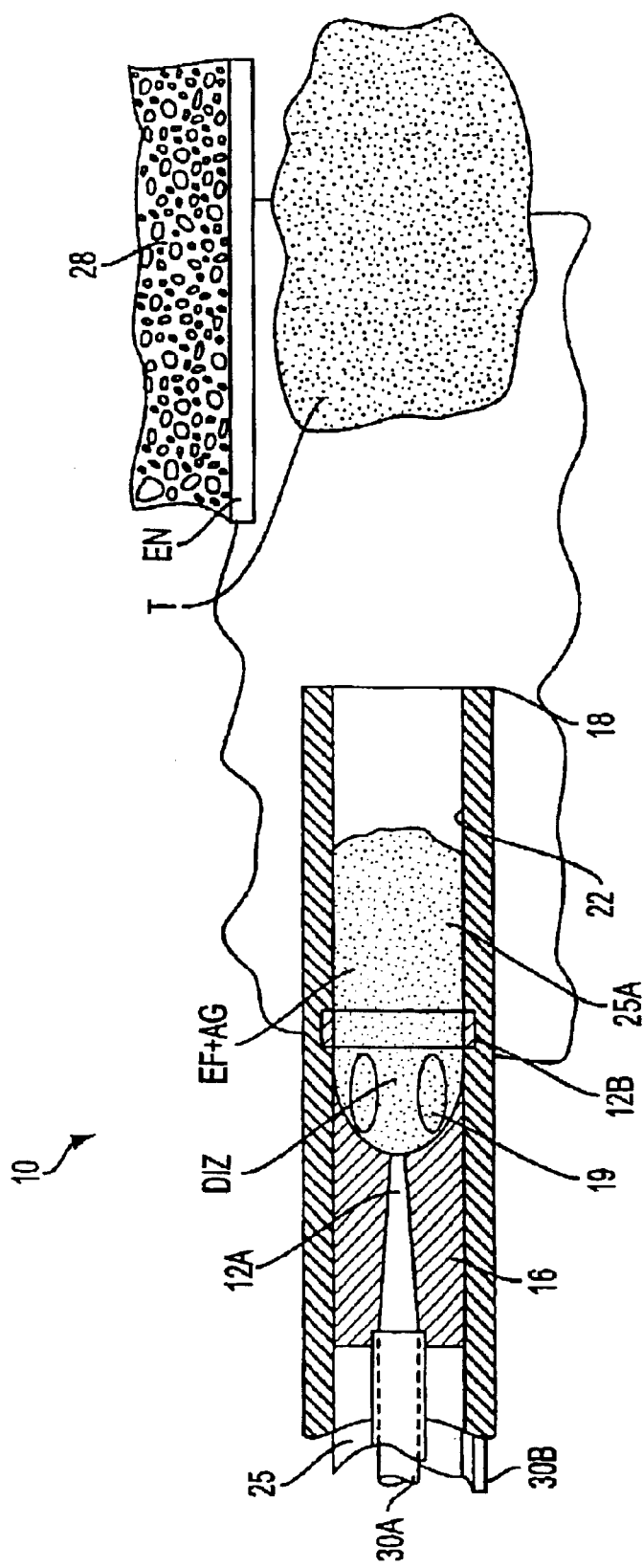

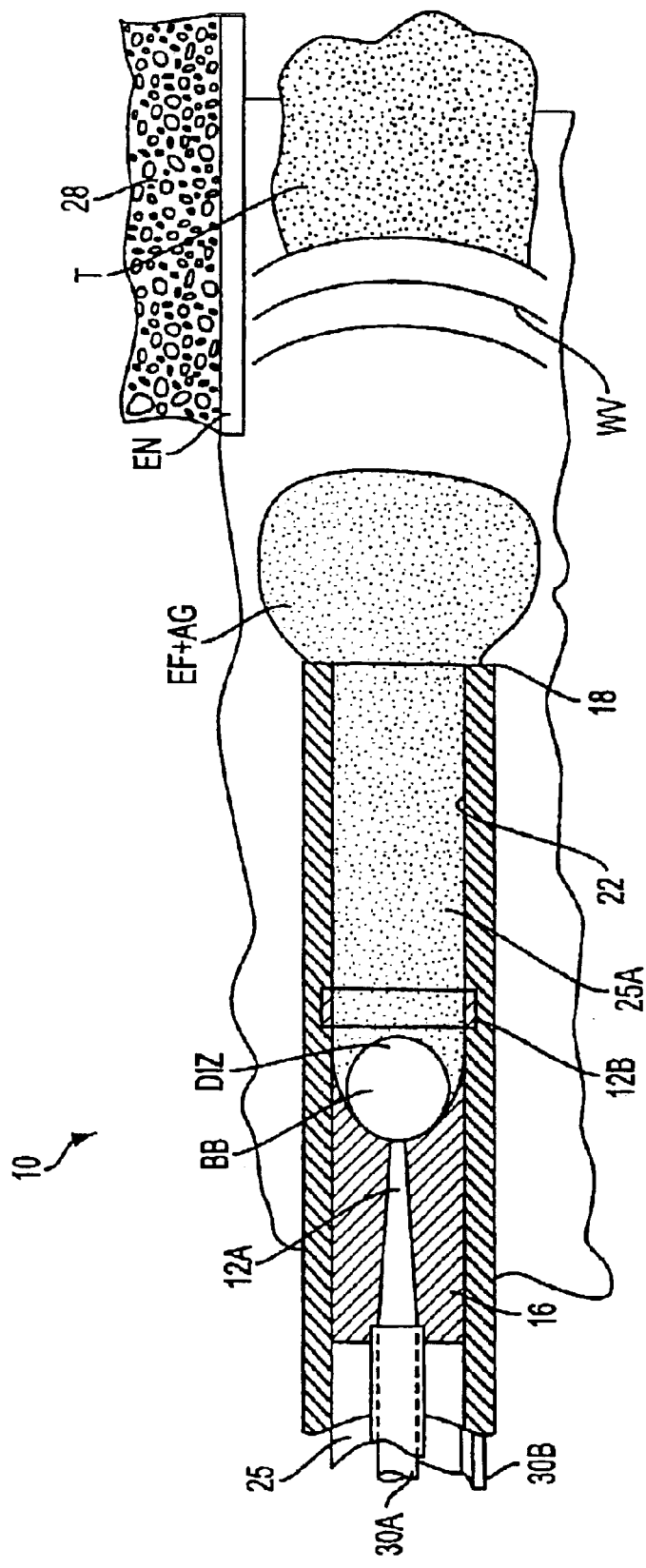

AT TIME = T+2 a.u.

MEDICAL INSTRUMENT WORKING END AND METHOD FOR ENDOLUMINAL TREATMENTS

CROSS-REFERENCE TO RELATED APPLICATIONS

This application is a continuation-in-part of U.S. patent applications Ser. No. 09/782,649 filed Feb. 12, 2001, now U.S. Pat. No. 6,508,816 titled "Medical Instrument Working End Creating Very High Pressure Gradients", which is a continuation-in-part of Ser. No. 09/181,906 filed Oct. 28, 1998, now U.S. Pat. No. 6,210,404 both of which are incorporated herein by this reference.

BACKGROUND OF THE INVENTION

1. Field of the Invention

The invention relates to the working end of a micro-catheter or other device for endoluminal introduction that utilizes a thermal energy emitter to apply energy to a fluid media within at least one interior bore of the working end to vaporize and/or cavitate the fluid and to eject the fluid media from the working end to apply energy to endoluminal structure in the form of therapeutic heat and/or acoustic energy.

2. Description of the Related Art

Varicose and spider veins are enlarged, dilated, and tortuous veins that are caused by weakness in the vein walls and incompetent vein valves. When the valves cease to function, the blood does not flow as effectively to the heart as it should but, rather, allowed to pool in the veins. This increases pressure in the vein and eventually causes the vessel walls stretch and distend. The vein increases in diameter and cannot return to normal size or shape.

In the prior art, catheter devices are used to apply radio frequency energy to vessel walls to cause ohmic heating therein which can damage and occlude the vessel. One disadvantage of commercially available Rf devices is that ohmic heating can easily damage nerves in the leg that extend along the exterior of varicose veins. New instruments and methods of energy delivery are needed for closure of blood vessels to treat varicose veins.

In the treatment of thrombus in a blood vessel, either in cardiac patients or stroke victims, conventional treatment is the intravenous administration of pharmacologic agents, such as t-PA (tissue plasminogen activator), streptokinase or urokinase. In such intravenous drug deliveries, the probability of success may be less than about 50 percent, and the success rates are limited by the fact that agents are not delivered directly to the site of the thrombus. To ablate thrombus in an invasive procedure, various energy-based catheters have been developed, for example utilizing laser and ultrasound energy delivery systems. A disadvantage of such approaches is that the catheter's diameter may be too large, and the catheter's flexibility may be limited, thus preventing the catheter's working end from reaching the thrombus site in the small circulatory arteries of the patient's brain. New catheters and methods of energy delivery are needed for disrupting thrombus.

SUMMARY OF THE INVENTION

In general, the invention comprises a flexible micro-catheter device or other member for endoluminal introduction that carries a thermal energy emitter, for example first and second electrodes coupled to an electrical source, within at least one interior bore of the device's working end. In one embodiment, electrical discharges between opposing polarity electrodes are adapted to vaporize, cavitate and expand a fluid media that inflows into and though the interior bore. The working end is adapted for related methods of use in Type "A" and "B" embodiments. The Type "A" embodiment is designed to deliver energy to endovascular media predominantly in the form of acoustic waves for disrupting thrombus. The Type "B" embodiment is designed to deliver energy to endoluminal media in the form of controlled therapeutic heat, without ohmic (resistive) heating of tissue as in practiced in prior art Rf devices.

In one embodiment of the Type "A" system, an electrical discharge in an interior lumen of the working end creates cavitation bubbles in an inflowing fluid media. The vapor media is ejected from the working end the expansion and collapse of such cavitation bubbles at high repetition rates will create acoustic waves that propagate distally from the working end to disrupt thrombus. The expansion and collapse of such cavitation bubbles also can be used to project or jet a pharmacological agent at a controlled velocity into the acoustically disrupted thrombus to further depolymerize the thrombus allowing it to flow though the patient's circulatory system. The system includes a computer-controller and various subsystems that allow for independent modulation of all parameters of electrical discharge and fluid media inflows to tailor the energy effects to dissolve thrombus rapidly since the passage of time is critical in treating victims of stroke. It is believed that there are wide variations in thrombus size, location and other patient-specific characteristics that will require many different treatment parameters, which are offered by the control systems of the invention. With respect to the electrical discharge source, the computer controller and software can independently modulate voltage, peak power per pulse, discharge pulse length, the energy profile within each discharge pulse, and the timing between discharge pulses resulting in a set or variable discharge pulse rate.

In a Type "B" system corresponding to the invention, electrical energy again is delivered to interior lumen of the working end that interfaces with pressurized fluid media inflows. In this embodiment, the working end is optimized for therapeutically heating the vessel walls to shrink, occlude or seal the lumen. One use of the Type "B" system is for closure of blood vessels to treat varicose veins. The working end causes controlled thermal effects in the vessel walls by means of superheated vapor that is propagated from the working surface. Advantageously, the peak temperatures cannot exceed about 100° C. which will prevent damage to nerves that extend along targeted vessels. Such nerves can easily be damaged if Rf energy and ohmic heating are used to obliterate blood vessels to treat varicose veins.

The Type "B" system and its method of use also can be used to apply therapeutic heat to vessel walls to treat chronic vascular insufficiency (CVI) or to shrink arterial vascular malformations (AVM) and aneurysms. The Type "B" system and method also can be used to apply therapeutic heat to any duct, cavity, lumen, septae or the like in the body to shrink, collapse or damage the anatomic walls or to fuse together and seal endothelial layers thereof

BRIEF DESCRIPTION OF THE DRAWINGS

FIGS. 3A–3C are sectional representations of the working end of FIG. 1 in a vessel lumen showing isotherms created in intraluminal fluids over a period of milliseconds following an electrical discharge between the first and second electrodes; FIG. 3A showing the typical isotherms at about the instant of electrical discharge which creates a gas bubble; FIG. 3B showing isotherms ns following the discharge when the gas bubble collapses into a cavitating volume and being ejected from the confinement of the recessed lumen; FIG. 3C showing isotherms several ns later with the cavitating volume being further ejected and cooling significantly.

FIGS. 6A–6D are illustrations that represent the manner of using the micro-catheter of invention to perform the techniques of the invention in dissolving thrombus; FIG. 6A being the working end advancing toward the thrombus; FIG. 6B being the working end after the start of introduction of an electrolytic pharmacologic agent into the working end; FIG. 6C being the working end at about the instant of electrical discharge showing acoustic energy delivery to disintegrate thrombus; FIG. 6D being the working end at ns after FIG. 6C showing the combination of acoustic energy delivery and pharmacologic agent jetting against the thrombus and the technique of "continuously" operating the acoustic and agent delivery systems while advancing the working end through the dissolving thrombus.

DETAILED DESCRIPTION OF THE INVENTION

Figure 1:
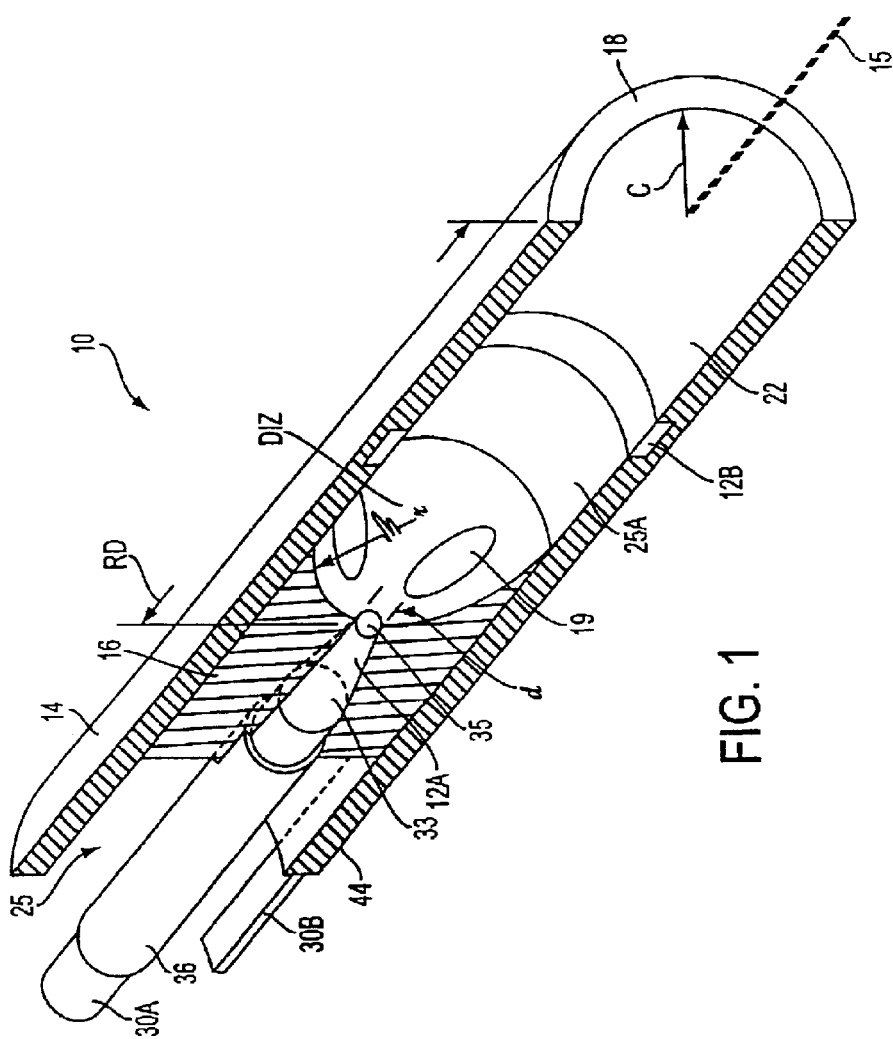
FIG. 1 is an enlarged sectional perspective view of a Type "A" micro-catheter working end of the invention showing the pharmacologic agent delivery lumen and first and second electrode geometry.

1. Type "A" Embodiment of Micro-Catheter. Referring to FIG. 1, the present invention comprises a micro-catheter system 5 having a body diameter of from 0.5 mm. to 2.5 mm. (not limiting) adapted for insertion into and through blood vessels as small as 1 mm. for accessing the site of thrombus in circulatory arteries of the brain of a stroke patient. In FIG. 1, the working end 10 of micro-catheter 5 is shown that carries an electrode arrangement with first and second electrodes 12A and 12B for pulsed electrical discharges therebetween. The electrical discharges are adapted to develop and expand gas bubbles BB that collapse into a cavitating volume CV within an electrolytic fluid composition EF including a pharmacologic agent AG introduced into the working end. The expansion and collapse of such gas bubbles at a repetition rate creates acoustic waves that propagate distally to disrupt or disintegrate thrombus. (The terms disrupt, disintegrate and fragment in relation to thrombus may be used interchangeably in this disclosure and are defined as meaning the reduction of a thrombus mass into a particulate-sized composition that will flow along with blood through the patient's circulatory system). The rapid expansion of such gas bubbles further develops pressure gradients in the cavitating volume of the electrolytic fluid EF to thus project or "jet" the cavitating volume CV at suitable velocities relative to the working end 10 and against and into acoustically-disrupted thrombus.

The catheter body or sleeve 14 is elongate and has any suitable length along centerline 15 (FIG. 1). The catheter body 14 is of any suitable extruded plastic catheter material or other braided or composite material known in the art. FIG. 1 shows first (proximal) electrode indicated at 12A along centerline 15 in distal catheter core 16 that is carried at recessed dimension RD from the distalmost end or perimeter 18 of catheter body 14. One or more fluid flow passageways 19 are provided through or around core 16 for allowing electrolytic fluid composition EF and pharmacologic agent AG flow therethrough. Catheter core 16, as can be seen in FIG. 1, has a concave-shape 20 facing distally for reasons described below. Second (distal) electrode 12B is shown as extending around the inner portion of walls 22 around the distal portion of the catheter's lumen 25, or more particularly, the distal recessed lumen portion indicated at 25A. It should be appreciated that second electrode 12B may comprise one or more separate electrode elements around the distal portion or end of catheter body 14.

Referring still to FIG. 1, it can be seen that the concave-shape indicated at 20 may be of any suitable radius r given the small dimension of recessed lumen portion 25A and of catheter body 14. It should be appreciated that the radius r of concavity (e.g., the concavity may be almost flat or flat) is less important than the fact that concavity 20 is recessed in lumen portion 25A a particular recessed dimension RD which ranges from a maximum of about 10.0 mm. to a minimum of about 0.5 mm. More preferably, the recessed dimension RD ranges from a maximum of about 5.0 mm to a minimum of about 1.0 mm. The recessed core 16 (which carries first electrode 12A) together with recessed lumen 25A are adapted to serve several purposes that are described next, and in additional relevant detail in Section 2 concerning the technique of the invention. The electrical discharge between the first and second electrodes causes several energy "effects", each of which must be modulated to achieve dissolution of thrombus while at the same time not damaging the endothelium EN or vessel walls 28 (see FIG. 2A). The energy "effects" resulting from a single electrical discharge, or preferably a sequence of pulsed discharges, in an electrolytic fluid medium in which the working end is immersed are: (i) the electro-mechanical (or hydraulic) effects which result in acoustic waves propagating within intraluminal fluids of a vessel; (ii) electro-thermal effects in the electrolytic fluid; and (iii) cavitation and propagation of fluids at high acceleration rates and fluid flow velocities away from the site of the electrical discharge.

Figure 2A:
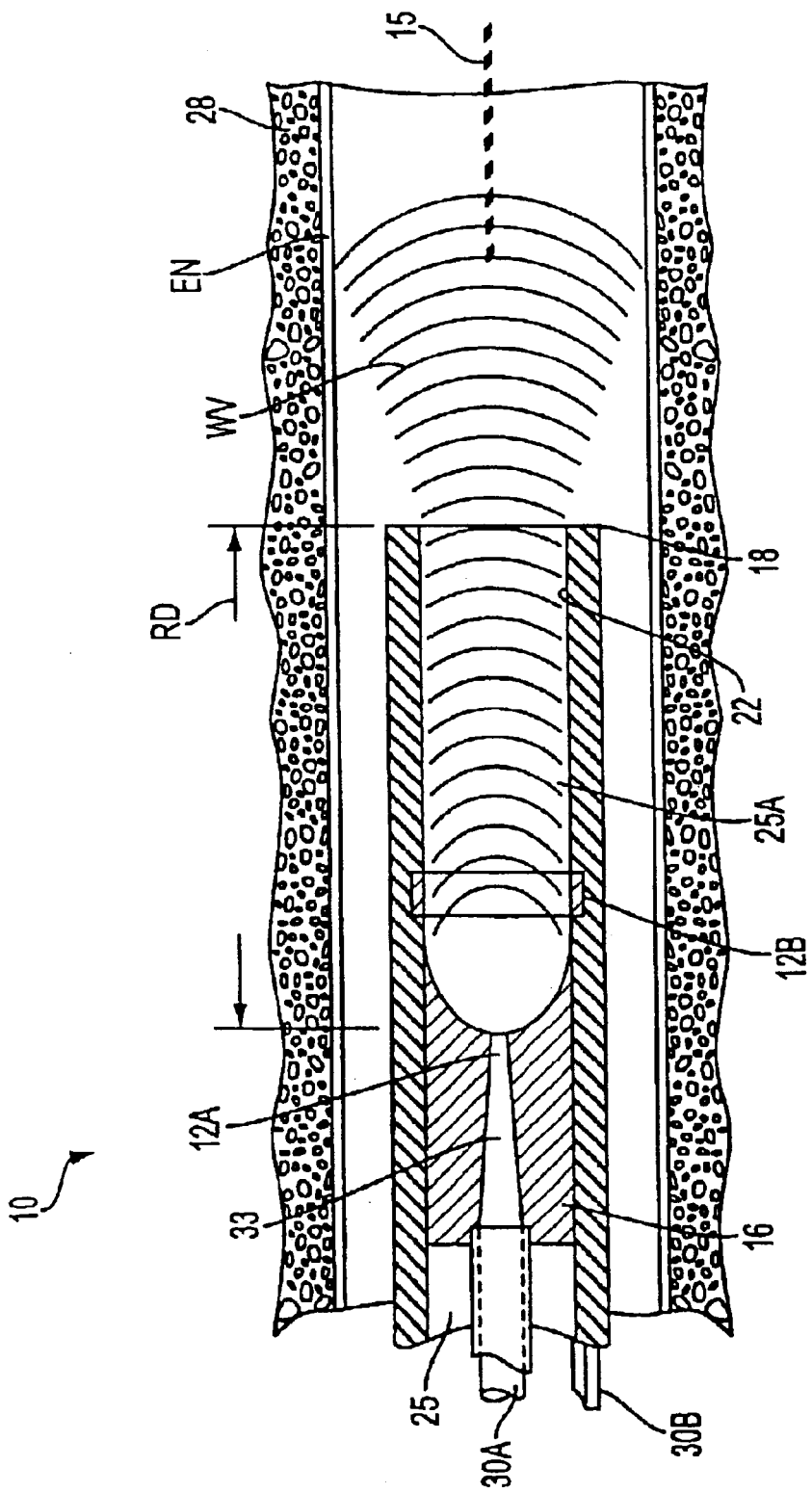
FIG. 2A is a sectional view of the working end of FIG. 1 illustrating that the recessed distal lumen will induce the propagate of acoustic waves generally axially in a vessel lumen rather than against the endothelium of the vessel.
Figure 2B:
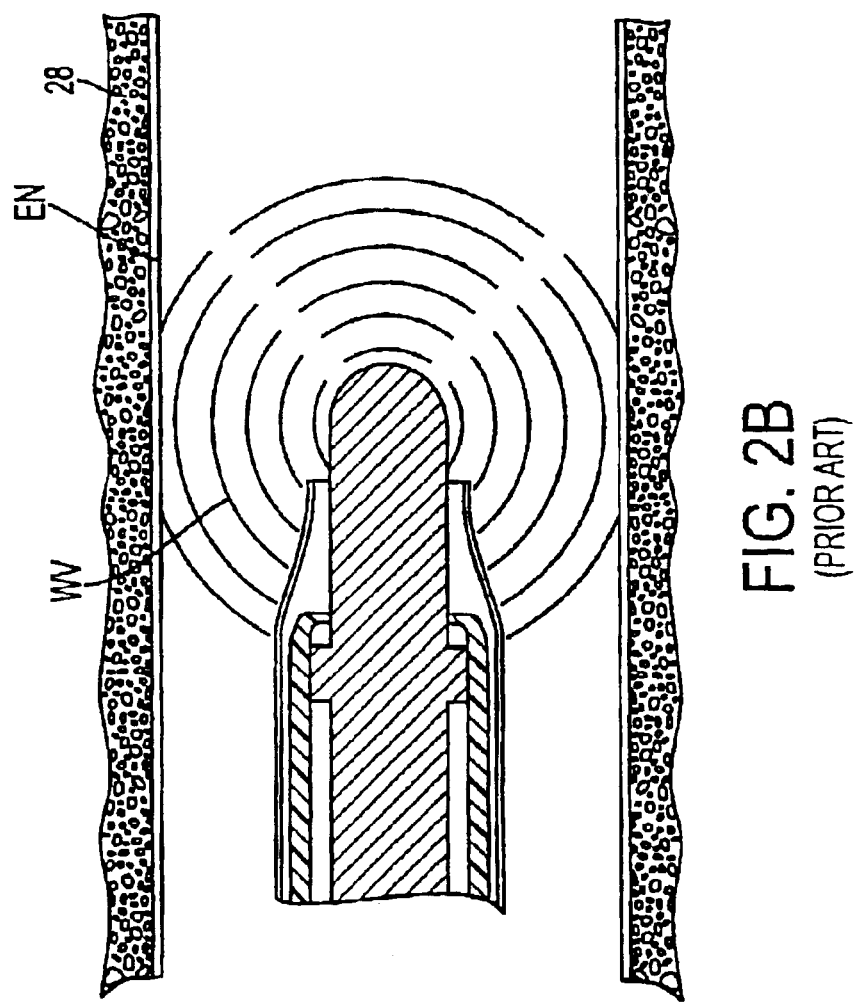
FIG. 2B is a prior art ultrasound "radiator" that propagates acoustic waves at all angles including direct angles against the vessel walls such that the endothelium may be damaged.

A first purpose for core 16 being recessed dimension RD is to provide means for directing acoustic wave propagation. Referring to FIG. 2A, acoustic waves WV are generated by the expansion and collapse of a gas bubble BB in contact with electrode 12A at the time of an electrical discharge. As will be described below, acoustic waves of a suitable frequency, either pulsed or continuous, can disrupt or fragment thrombus (cf. U.S. Pat. No. 5,424,620 to Rosenschien titled "Ablation of Blood Thrombi By Means of Acoustic Energy"). The extension of recessed lumen portion 25A distally from electrode 12A is adapted to initially confine the expansion and collapse of gas bubbles to the working end. Such confinement within the walls 22 around lumen 25A thus direct all hydraulic forces and acoustic wave forms WV generally axially and distally along axis 15 as indicated in FIG. 2A. In other words, the propagation of such waves within intraluminal fluids (e.g., blood or an introduced fluid) will be generally "along" the vessel walls 28 instead of more directly against the vessel walls. Such an axial propagation of wave forms WV is important because damage to the endothelium EN or perforation of the vessel wall could result in a life-threatening complication. The "along-the-lumen" acoustic wave propagation that is provided by the working end 10 of the invention is to be contrasted with the prior art ultrasound catheter of FIG. 2B in which the exposed "radiator" may propagate acoustic waves at more direct angles against the vessel walls and thus have a higher probability of damaging the endothelium EN or bursting the vessel wall.

Figure 3A:
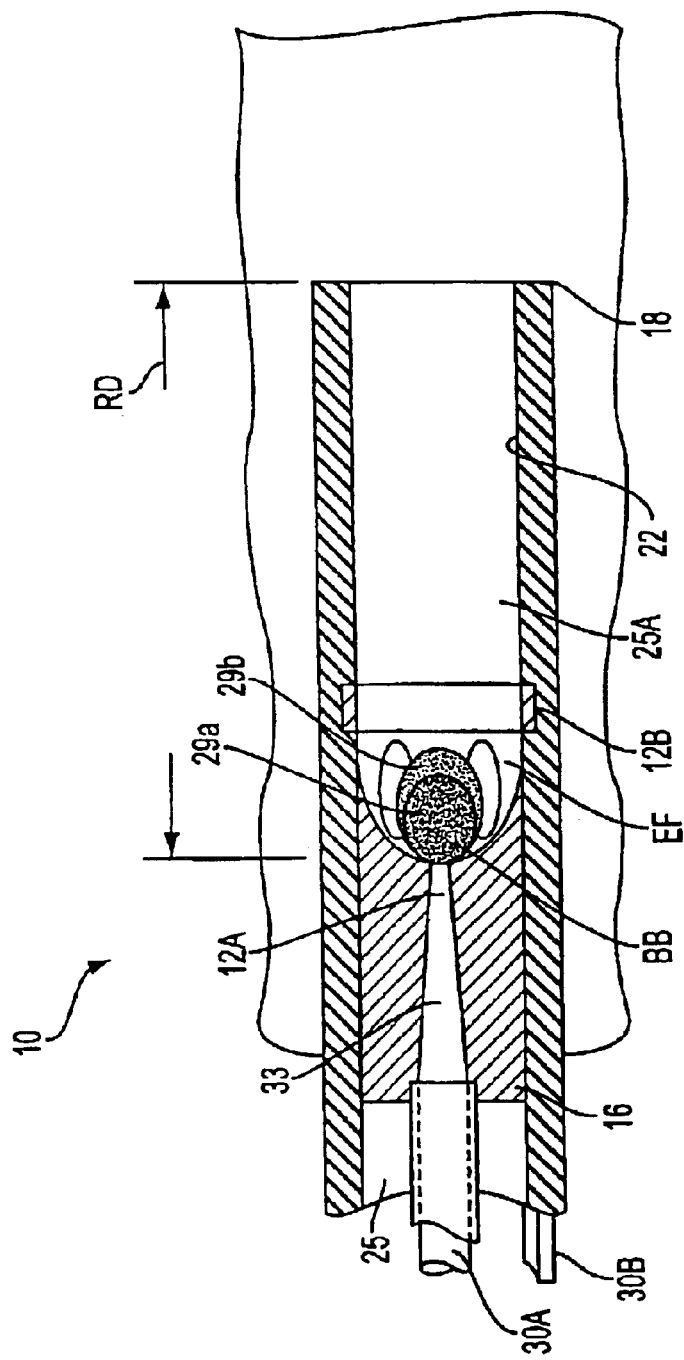

A second purpose for core 16 and first electrode 12A being recessed dimension RD is to provide thermal-effect dissipation means to eliminate the possibility of tissue damage from thermal effects caused by the electrical discharge. It is an objective of the invention to dissolve thrombus without relying on thermal energy being applied to the thrombus itself. For this reason, the extended lumen portion 25A of the above described dimensions is provided to largely confine thermal effects to the introduced electrolytic fluid composition EF (or blood) between electrodes 12A and 12B. Thus, thermal effects will not be in close proximity to the endothelium EN or vessel walls 28. Referring to FIGS. 3A–3C, representations of isotherms 29a–29c are shown within and around working end 10 in electrolytic fluid EF and indicate temperature levels in the fluid in which the working end 10 is immersed. The views of FIGS. 3A–3C are at various arbitrary nanosecond (ns) intervals after an electrical discharge between electrodes 12A and 12B. The temperature levels within the isotherms 29a–29c are arbitrarily labeled with the darkest shading indicating a "tissue-ablative" temperature range, the medium shading being a temperature range creating "negligible tissue trauma", and the lightest shading being a temperature range that has "no effect" on tissue. FIG. 3A represents fluid EF within at the time of an electrical discharge (at time=$T_{ZERO}$) showing the superheating of the electrolyte to about 100° C. in contact with electrode 12A and the formation of a gas or cavitation bubble BB which comprises the highest temperature zone and which would ablate the endothelium EN if in contact with it. FIG. 3B represents the effect of the discharge a few ns later (at time=$T_{+1\ a.u.}$ where a.u. is an arbitrary unit of time) at which time the cavitation bubble BB would collapse into a volume of smaller cavitating bubbles (not shown; hereafter cavitating volume CV) with the superheated area expanding and moving away from electrode 12A caused by pressures related to the bubble expansion and collapse. FIG. 3C represents the effect of the electrical discharge a few ns later (at time=$T_{+2\ a.u.}$) wherein the superheated region has moderated in temperature as the cavitating volume CV expands further and is projected distally from the working end of the catheter. Thus, it can be seen in FIG. 3C that the endothelium EN and vessel walls 28 can be protected from thermal effects by confining the electrolytic fluid EF when superheated to recessed lumen portion 25A. By the time that the electrolytic fluid EF is ejected from the lumen portion 25A, it is believed that the dimension RD of lumen 25A will allow for cooling of the cavitating volume to a non-damaging temperature. For this reason, a time-temperature gradient can be developed which will show a dissipation-of-temperature zone indicated at shaded region $D_T$ wherein the temperature of the fluid EF would be cooled below the threshold level that would damage tissue. As will be described below in the technique of the invention, all energy delivery parameters (voltage, current, discharge rate, electrolytic level of fluid, etc.) will be tested in various combinations to place $D_T$ zone at a suitable location at or about the distal end 18 of the catheter.

Figure 4:
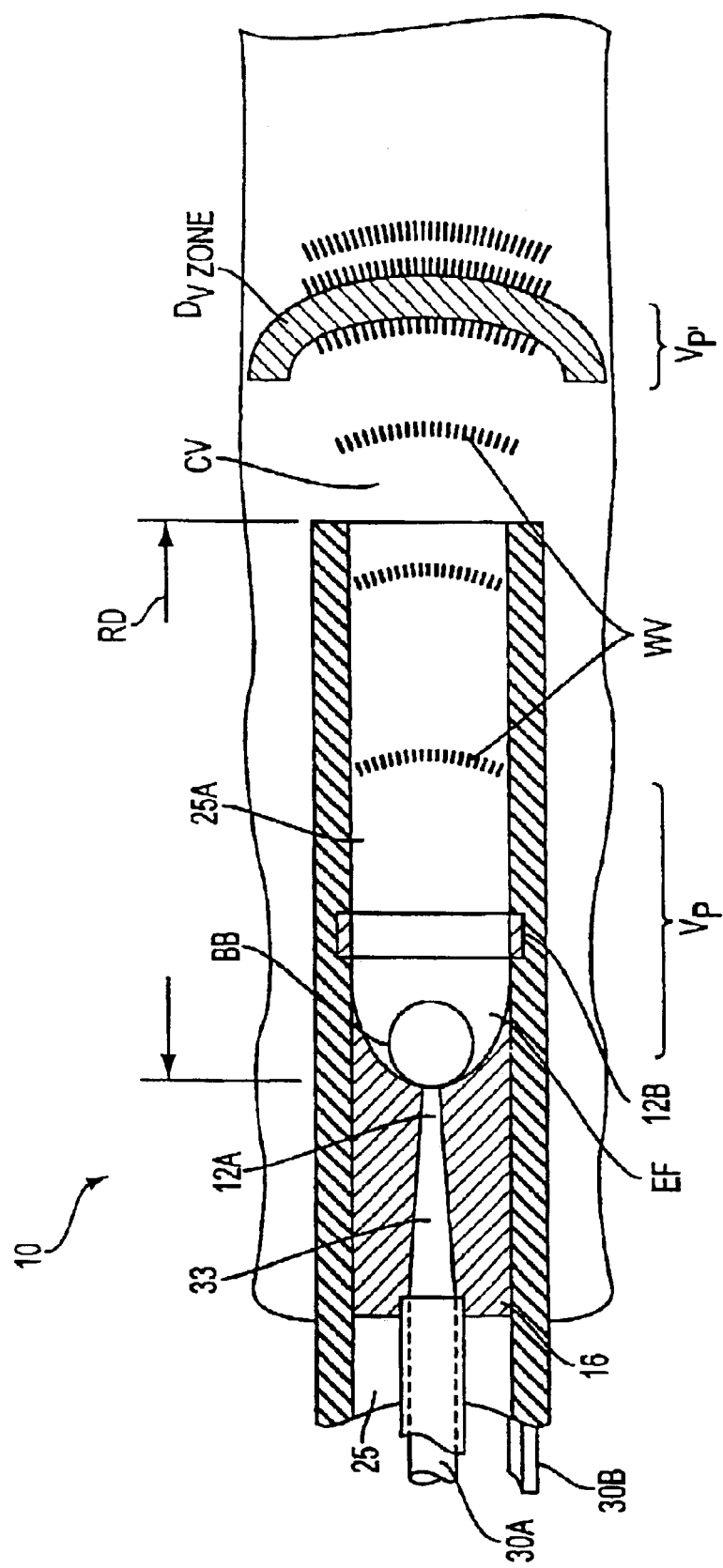
FIG. 4 is sectional representations of the working end of FIG. 1 in a vessel lumen showing velocities of ejection of an introduced fluid over a period of milliseconds following an electrical discharge between the first and second electrodes.

A third purpose for working end core 16 being recessed by dimension RD is to provide fluid-velocity dissipation means for reducing the velocity of fluid jetting from working end 10 to a suitable velocity that will not "cut" tissue. The extended lumen portion 25A is provided as a region of confinement within the device in which the acceleration in propagation of the cavitating volume CV is slowed such that it will not contact the endothelium EN at any particular high velocity that would cut the endothelium. It should be understood that the velocity of propagation of the cavitating volume CV (including pharmacologic agent AG) relates to (i) the pressure under which the fluid is introduced, and (ii) the expelling forces created by the expansion and collapsed of gas bubbles. Further, the jetting velocity of the cavitating volume into the interface of intraluminal fluid (blood) makes somewhat unpredictable the actual distal movement of the cavitating volume CV. In any event, the velocity of propagation of the cavitating volume CV is different from the speed of propagation of acoustic waves WV therein which propagate across the interface between the introduced fluid EF and the pre-existing intraluminal fluids (blood). The objective of the working end of the present invention is to create a flow velocity in the cavitating volume, which includes the introduced pharmacologic agent AG, to engulf the thrombus instantly after the acoustic waves have struck and disrupted the thrombus. At the same time, the flow velocity must not be so high as to cut tissue. As is well known in field of laser-tissue interactions, such soft tissue cutting occurs when short laser pulses causes the explosive expansion of media absorbing photonic energy in close proximity to tissue, or within fluids in the tissue surface itself, thus creating cavitation within the media or tissue. In such laser-tissue interactions, any soft tissue proximate to the expansion and collapse of such bubbles will be disrupted or "cut". A similar cutting process could occur with the fast electrical discharge between electrodes 12A and 12B of the working end 10 disclosed herein if any such tissues were proximate to first electrode 12A. Since the objective of the present invention is to not cut tissue, it is necessary to insure that thrombus T and the vessel walls 28 are maintained at a particular desired distance from the cavitating volume CV and its distal projection at particular velocities. As shown in FIG. 4, the velocity of propagation $V_P$ of the cavitating volume or agent AG is generally indicated by wave forms WV. The distance between wave forms indicates velocity, or the distance traveled per arbitrary unit of time, which diminishes as distance increases from the location of bubble formation at electrode 12A. FIG. 4 thus indicates that initial $V_P$ close to electrode 12A will diminish to lesser $V_P'$ just beyond the distalmost end 18 of the catheter. It can be thus understood that electrode 12A and extended lumen portion 25A are provided to insure that tissue is not in close proximity to a cavitating volume CV when it is traveling or jetting distally at initial $V_P$ which could cut tissue. Still, thrombus T contacted by the cavitating volume CV at diminished velocity $V_P'$, in addition to being subjected to acoustic wave forces sufficient to fragment thrombus T, will be engulfed in chemical lysis effect of the pharmacologic agent AG within the cavitating volume CV as described below. For this reason, a time-velocity gradient can be developed to identify a dissipation-of-velocity zone indicated at shaded region $D_V$ wherein the velocity of electrolyte or agent jetting would be below the threshold level that would "cut" tissue. The discharge parameters (voltage, current, discharge rate, electrolytic level of fluid, etc.) will be tested in combinations to place $D_V$ zone at a suitable distance from the distal end 18 of the catheter A fourth purpose for the recessed dimension RD of core 16 is to provide a confinement zone or discharge interaction zone DIZ in which the inner surfaces of walls 22 around recessed lumen portion 25A are adapted to capture the introduced electrolytic fluid EF between electrodes 12A and 12B. By this means of largely capturing the electrolytic fluid EF momentarily before it intermixes with the pre-existing intraluminal fluids, it is possible to accurately predict and model the effects of the electrical discharge since the electrolytic characteristics of the electrolytic fluid FF can be pre-determined. This is to be contrasted with a situation in which no means would be provided for confining a known electrolyte between the electrodes and the discharge would occur in blood or a mixture of blood and introduced fluids, in which case the effects would be unpredictable.

A fifth purpose for working end core 16 being recessed by dimension RD is to provide electrical discharge confinement means for reducing the threshold energy levels required to induce cavitation bubble formation—that is, to increase energy efficiency. It is postulated that the threshold for bubble generation per electrical discharge (and thus acoustic wave propagation) will be in the range of about 1 $\mu J$ to 50 $\mu J$ which may be significantly less than used in laser-based catheters developed for angioplasty purposes. (As described below, a somewhat broader range of $\mu J$ energy delivery is disclosed to perform the technique of the invention). It is believed that the faces of walls 22 around recessed lumen portion 25A and the capture of the expanding bubble volume will create additional pressures on the bubble formation and thus lower the threshold energy discharge requirement, in contrast to a situation in which no such confinement was provided.

Figure 5:
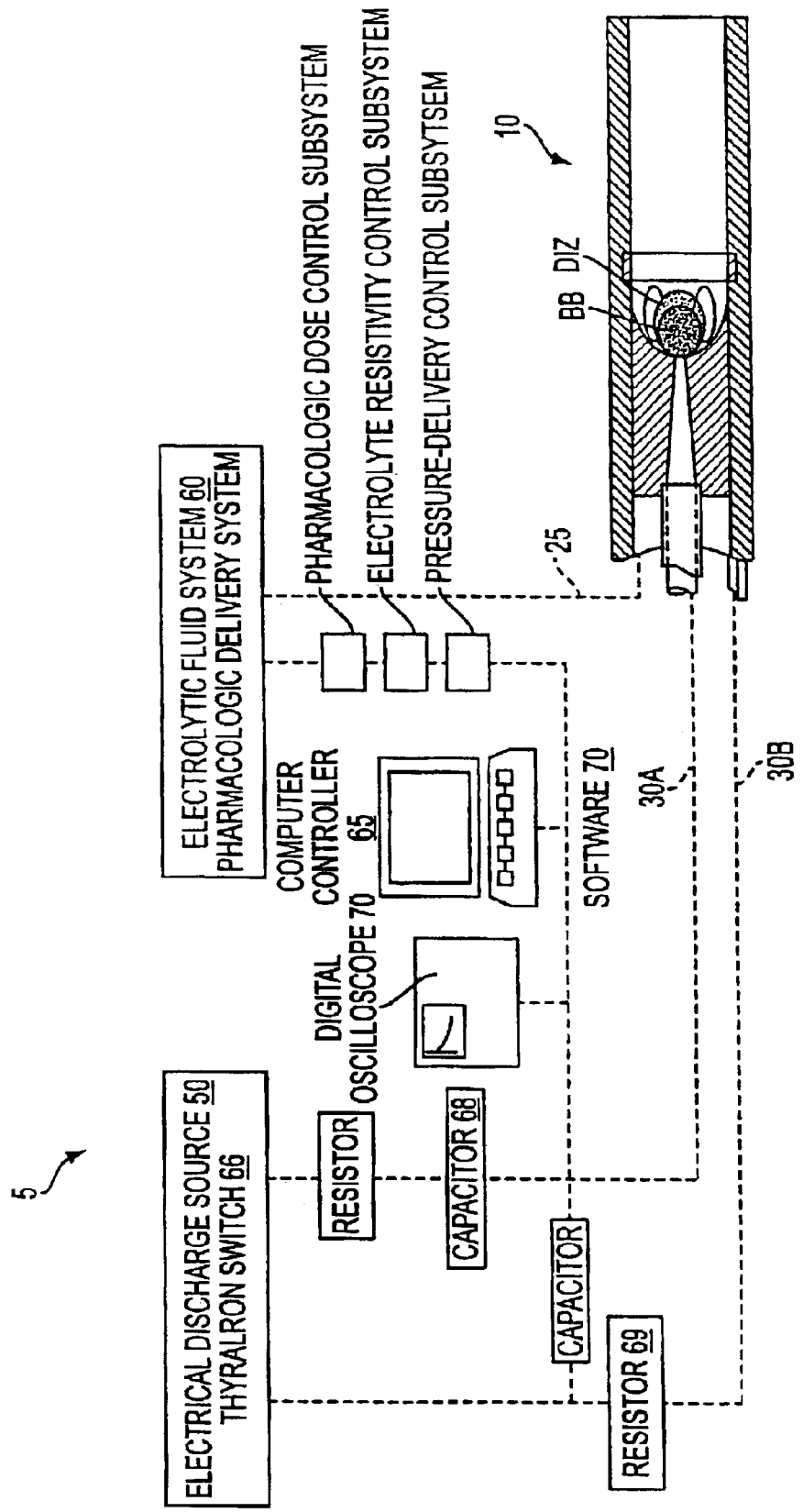
FIG. 5 is a schematic view of the electrical discharge source and pharmacologic agent delivery source of the invention, together with computer-control systems for modulating all parameters of combined electrical discharge and agent delivery to optimize thrombus dissolution.

Referring to FIGS. 1 and 5, first proximal electrode 12A is coupled to the distal end of conductive wire or element 30A that extends through lumen 25 of catheter body 14. The recessed catheter core 16 is bonded or molded in place within lumen 25 of the catheter with electrode 12A molded or inset therein. To catheter distal core 16 may be any suitable insulated material such as a plastic or glass-type compound. First electrode 12A, as can be seen in FIG. 1, has a significantly reduced cross-section portion 33 such that the exposed electrode surface portion 35 that is exposed to a discharge in recessed lumen 25A has a very small diameter d (e.g., ranging in diameter from about 5 microns to 25 microns or equivalent cross-section). The exposed surface area 35 preferably is from about 0.05 mm$^2$ to 0.5 mm$^2$ and thus causes the energy discharge to be focused about a very small surface area within the discharge interaction zone DIZ. FIG. 1 shows that wire 30A with insulation 36 may be carried loosely and lumen 25 of catheter sleeve 14 making the catheter simple to fabricate. Current-carrying wire 30A may be any suitable conductive material, for example platinum, copper, gold, etc. In FIG. 1, it can further be seen that the medial portion of catheter body 14 has wall portion 44 with current-carrying flat wire 30B embedded therein which extends to second electrode 12B. The thickness of wall 44 may be any suitable dimension. Wires 30A and 30B may be any diameter from about the 10 to 200 microns in diameter or equivalent cross-section. The axial dimension between first electrode 12A and second electrode 12B ranges between about 0.1 mm. and 10.0 mm., along with a lumen cross-section indicted at C in FIG. 1 ranging between 0.2 mm. and 2.0 mm. in diameter or equivalent cross-section thus creating a particularly dimensioned discharge interaction zone DIZ.

FIG. 5 is a schematic view of the catheter system 5 showing electrical discharge source 50 and the electrolytic fluid composition EF and pharmacologic agent AG delivery system 60 that are connected to working end 10 and lumen 25 at a catheter handle portion (not shown) by means known in the art. Typically, the fluid composition EF including agent AG are intermixed to provide a known electrolytic component (i.e., with known resistivity (Ohms/cm.), heat capacity (J/g.), etc.). The fluid delivery system 60 includes a manual control or preferably is controlled by a computer-controller known in the art and indicated at 65 to release the fluid from a reservoir operatively connected to the catheter handle. As can be seen in FIG. 5, the computer controller 65 coupled to the fluid delivery system 60 allows independent modulation of all elements of electrolytic fluid EF delivery through subsystems, including: (i) the dose of pharmacologic agent AG per volume of fluid EF; (ii) the electrolytic component (current-resisting or sensitizing composition yields resistivity of fluid EF in Ohms/cm.) of the fluid EF; (iii) the particular pressure of flow of fluid EF through the catheter and working end; and (iv) the timing of fluid EF introduction relative to the actuation of a pre-determined sequence of electrical discharges from electrical discharge source 50.

The electrical discharge source 50 of the invention also is shown in FIG. 5 and is based on a thyratron switch 66 that can enable a very fast discharge of capacitor 68. After the thyratron is switched on, and following a very short rise time, an electrical discharge pulse will be generated between first electrode 12A and second electrode 12B that results from the discharge of the capacitances through the electrolytic fluid EF that has flowed into distal lumen portion 25A and in which the discharge interaction zone DIZ is thus immersed. The electrical discharge source 50 and the wires 30A and 30B will have some capacitance which will result in the voltage at the electrodes 12A and 12B to be somewhat less than the starting voltage at capacitor 66. Still referring to FIG. 5, with the thyratron 66 switched off, the capacitor 68 will charge back to its potential through a second resistor and through the electrolytic fluid in which discharge interaction zone DIZ and working end 10 is still immersed. The electrical discharge source 50 is further is coupled to computer controller 65 that may be programmed with suitable software 70 to independently modulate all parameters of energy levels and timing the electrical discharge, including: (i) voltage, current and peak electrical power per pulse; (ii) the length of a discharge pulse; (iii) the profile of energy within each discharge pulse, and (iv) the timing between discharge pulses resulting in a set or variable discharge pulse rate. FIG. 5 shows that a digital oscilloscope 75 is between electrodes 12A and 12B to register the voltage and current pulses in association with computer controller 65.

2. Technique of Use of Type "A" Embodiment of Micro-Catheter.

Figure 6A:
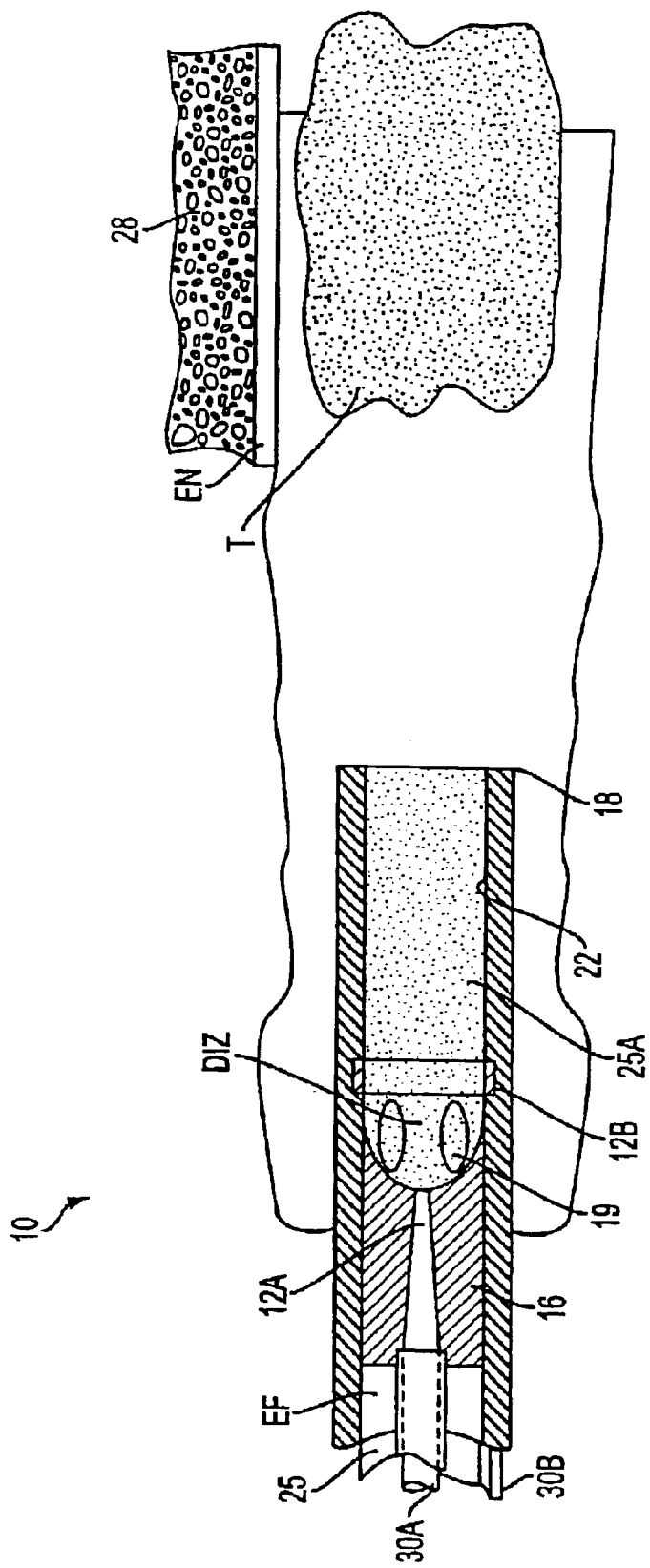

In use, the patient would be prepared in the usual manner and working end 10 of catheter 5 would be introduced to the site of the thrombus T in the blood vessel under any suitable imaging or angiography system. Referring to FIG. 6A, under such imaging, the working end 10 of the catheter would be advanced to within about 10 mm. or less from the location of thrombus T.

Next, referring to FIG. 6B, the controller 65 would be actuated (at time=$T_{ZERO}$) to deliver a predetermined dose of electrolytic fluid EF and pharmacologic agent AG through lumen 25 at a pre-selected pressure into recessed lumen portion 25A at the working end 10 of the catheter. The composition of electrolytic fluid EF (e.g., saline solution) and pharmacologic agent AG would have been determined prior to treatment by modeling as described above. The pharmacologic agent AG is selected from a class of suitable thrombolytic agents known on the art, for example, including t-PA, streptokinase and urokinase.

Now referring to FIG. 6C, at a certain time later (ranging from about a ms to 1 second) hereafter identified as an arbitrary unit of time a.u., the electrical discharge source 50 is actuated. FIG. 6B thus represents time=$T_{+1\ a.u.}$ when a first electrical discharge crosses the gap between first electrode 12A and second electrode 12B which superheats the electrolytic fluid EF in contact with surface area 35 of electrode 12A. In a matter of nanoseconds or less, the discharge forms a cavitation bubble BB that expands in diameter from a few microns to about 500 microns or the size of the lumen. The expansion of the bubble within recessed lumen portion 25A will develop pressure waves or acoustic waves that will propagate distally within working end 10 and then through intraluminal fluid (e.g., blood) to strike the thrombus T as was illustrated in FIG. 2A. It is believed that the acoustic waves WV will resonate within the thrombus to thus disrupt or disintegrate the thrombus as shown in FIG. 6C. As also is shown in FIG. 6C, the expansion of the bubble BB causes the electrolytic fluid EF and agent AG to be ejected distally from the working end 10.

Figure 6D:
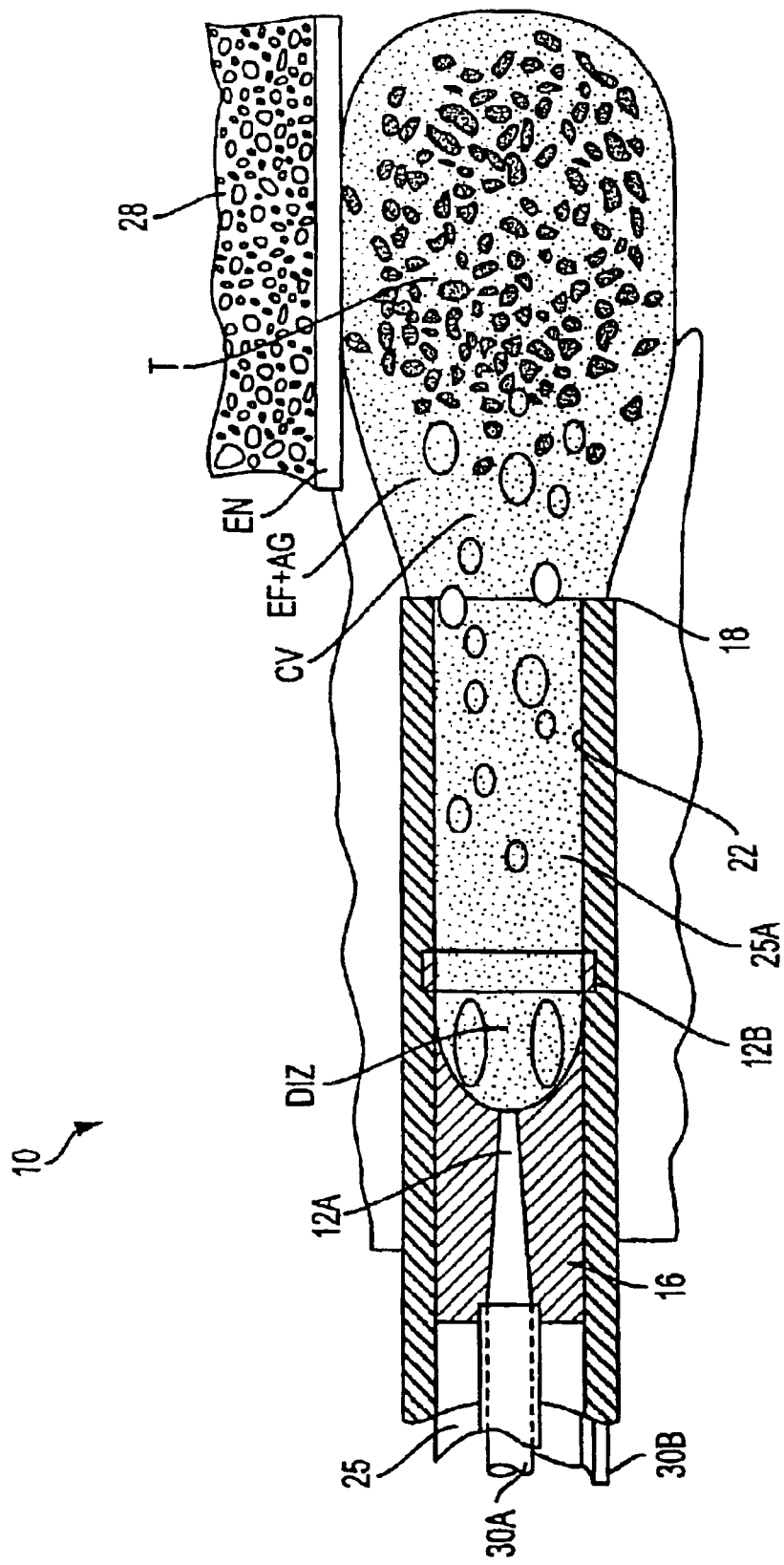

FIG. 6D at time=$T_{+2\ a.u.}$ represents the ejection or jetting of fluid EF and agent AG further to engulf the disintegrated or acoustically-disrupted thrombus T. It is believed that agent AG will be ejected distally with the velocity being enhanced by concave surface 20 such that the velocities within lumen 25A will range from about 1 to 25 m/s. As also shown in FIG. 6D, it is postulated that the energy parameters can be modulated to produce cavitation bubbles resulting from the collapse of initial bubble BB, and fluid velocities, that will dissipate entirely at distances ranging from about 0.1 mm. to 5.0 mm. from the distal end 18 of the catheter which would meet the objective of the invention. Not shown in FIG. 6D are follow-on pulsed electrical discharges that will repeat the process of acoustic wave generation and pharmacologic agent AG jetting. By this combination technique, it is believed that pressure waves WV against the thrombus T followed by the immersion of remaining thrombus in the cavitating pharmacologic agent AG will dissolve the thrombus T rapidly and efficiently to a particulate dimension that will flow through the patient's blood vessel system. It is believed such a combination technique will offer better thrombolytic results than possible with the use of energy-delivery alone, or the use of pharmacologic agents alone. The system disclosed herein is adapted to be tested with modulation of all electrical discharge parameters to define the optimal pulse rate for acoustic waves to disrupt thrombus, and the locations of dissipation zones as defined above to control fluid jetting velocities and thermal effects. Modeling suggests that the pulse energy that is optimal for thrombolysis, both for acoustic wave generation and fluid propagation is from about 5 µJ to about 500 µJ at pulse discharge repetition rates from about 1 Hz to 1 kHz. More preferably, the discharge repetition rates range from about 10 Hz to 500 Hz. Still more preferably, the discharge repetition rates range from about 50 Hz to 100 Hz.

It should be appreciated that slight variations in the technique are intended to fall within the scope of the invention, such as introducing the electrolytic fluid and pharmacologic agent AG under pressure from 1 to 30 seconds before actuating the electrical discharge to thus develop thrombolytic effects in advance of the acoustic wave propagation. Any sequence of such agent thrombolysis and electroacoustic waves are intended to fall within the scope of the inventive technique. While the invention is particularly adapted for small diameter circulatory arteries in the brain, it should be appreciated that the catheter may be used to dissolve thrombus in any part of the patient's circulatory system.

It should be appreciated that the working end of the present invention described above may be adapted for use with other energy delivery means, for example a laser source. The Type "B" embodiment would have a working end (not shown) that has all the similar dimensions as a Type "A" embodiment except that the laser source is provided to pump photonic energy along an optic fiber to recessed portion 25A (see FIG. 1). The photonic energy will then be absorbed by the introduced fluid which may be seeded with any suitable chromophore as is known in the art. Any suitable laser wavelength from about 100 nm to 3 microns, or even non-monochromatic light from a flashlamp, may be used at repetition rates from 1 Hz to 50 kHz with energy densities from 0.1 to 5.0 J/cm$^2$, with the preferred wavelength(s) being in the infrared portion of the spectrum that is absorbed in water of the seed fluid.

3. Type "B" Embodiment of Working End for Energy Delivery.

Figure 7:
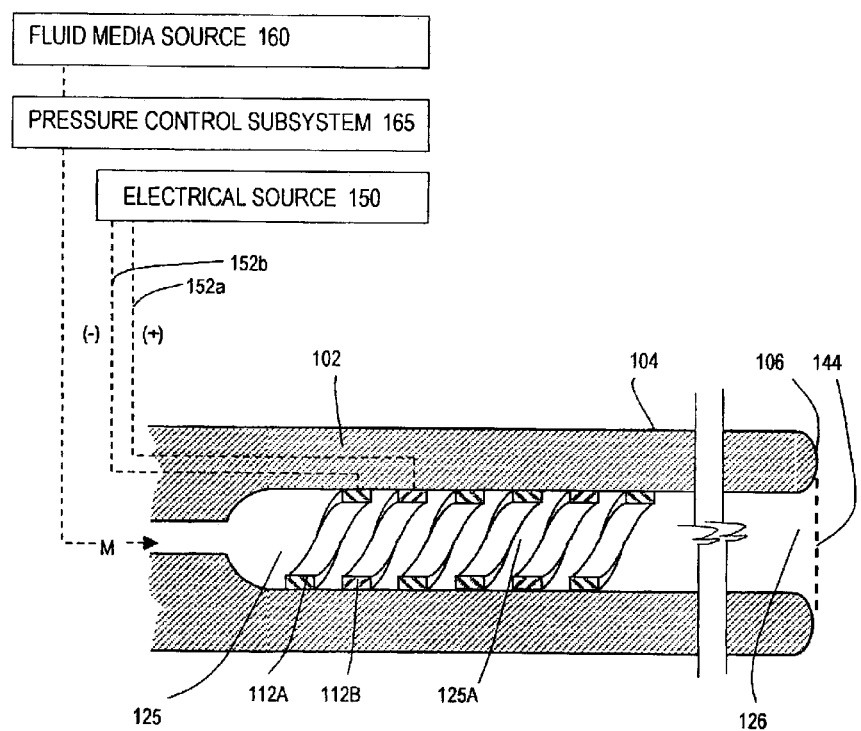
FIG. 7 is a sectional view of a Type "B" embodiment of an instrument working end for applying energy to tissue, and is more particularly for thermal treatment of endoluminal body structure.

Now referring to FIG. 7, an alternative Type "B" embodiment of instrument working end 100 is shown in sectional view. The previous Type "A" apparatus was optimized for controlling and limiting thermal effects in tissue. In this Type "B" embodiment, the system again utilizes a similar apparatus and again the thermal effects are controlled—but the application of energy is designed to cause a selected level of thermal effects in endovascular tissue, or in body media within or about other body lumens, ducts and the like.

FIG. 7 illustrates the working end 100 of a member or catheter body 102 that is dimensioned for introduction into a patient's vasculature or other body lumen. The diameter of body 102 can range from about 1 Fr. to 20 Fr. The working end 100 typically is carried at the distal end of a flexible catheter but may also be carried at the distal end of a more rigid introducer member. In a rigid member 102, the working end also can be sharp for penetrating into tissue or into the lumen of a vessel.

The working end 100 of FIG. 7 defines a surface 104 which extends about the radial outward surface of the member and the distal terminus 106. The working end again carries opposing polarity electrodes 112A and 112B as thermal energy emitters in an interior bore or lumen 125 that terminates in a media entrance port 126 in the distal terminus 106. The bore may be any diameter as described in the Type "A" working end above. In this embodiment, the electrodes 112A and 112B are spaced apart, indicated with (+) and (−) polarities, and configured in an intertwined helical configuration to provide a substantially large surface area for exposure to fluid media M. The electrodes can extend axially from about 1 mm. to 50 mm. This type of electrode arrangement will enhance energy delivery to the fluid to allow effective continuous vaporization thereof As shown in FIG. 7, the electrodes can be recessed into bore 125 from the distal end by any dimension ranging from about 10 microns to 100 mm. or more. The working end again defines a lumen portion 125A between the electrodes 112A and 112B wherein energy application is focused to create the desired energy density in the inflowing fluid media M, in this case to cause its immediate vaporization. The type of energy delivery provided by the working end 100 relates to controlled thermal effects. The superheated vapor is propagated across the interface 144 defined by the working surface 104 that carries the open port 126, which in this embodiment comprises the distalmost surface of member 102. It should be appreciated that the instrument may have a plurality of media entrance ports 126 in surface 104 of the member 102, for example to apply energy radially outward as well as distally.

In the system embodiment of FIG. 7, the electrodes 112A and 112B are coupled to electrical source 150 by leads 152a and 152b. The working end 100 also is coupled to fluid media source 160 that carries pressurization means of any suitable type together with a pressure control subsystem indicated at 165. Such systems operate as described in the Type "A" embodiment.

Figure 8:
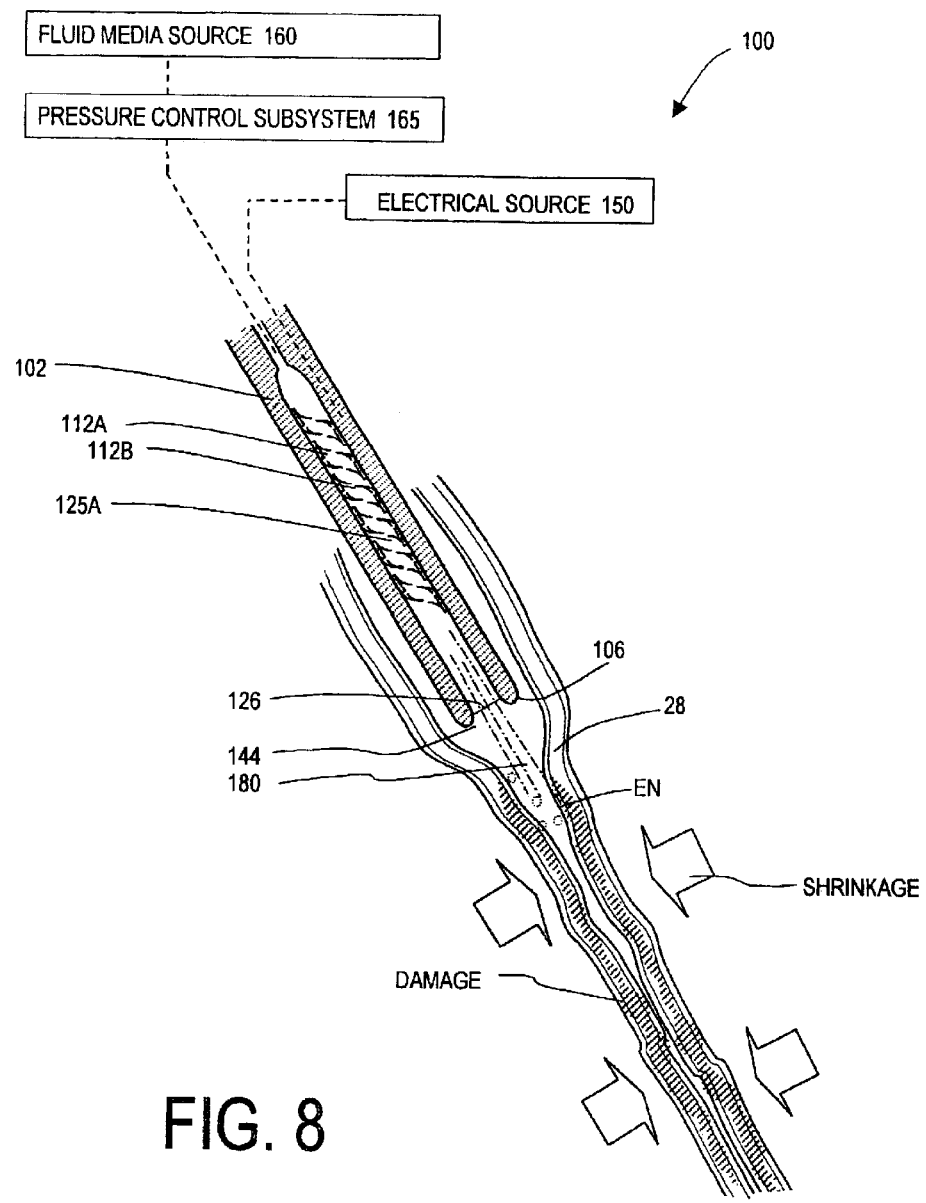
FIG. 8 is a sectional view of the instrument working end of FIG. 7 depicting a method of the invention in applying energy to tissue to cause thermal effects in an endoluminal environment.

In FIG. 8, the method of the invention is shown graphically wherein the distal end 100 is introduced into vasculature for the purpose of creating thermal effects in the vessel walls 28, its endothelial layer EN or blood. In one targeted endovascular procedure, as depicted in FIG. 8, the objective is to apply controlled thermal energy to tissue to shrink and/or damage vessel walls to treat varicose veins. Most endothelial-lined structures of the body, such as blood vessel and other ducts, have substantially collagen cores for specific functional purposes. Intermolecular cross-links provide collagen connective tissue with unique physical properties such as high tensile strength and substantial elasticity. A well-recognized property of collagen relates to the shrinkage of collagen fibers when elevated in temperature to the range 60° to 80° C. Temperature elevation ruptures the collagen ultrastructural stabilizing cross-links, and results in immediate contraction in the fibers to about one-third of their original longitudinal dimension. At the same time, the caliber of the individual collagen fibers increases without changing the structural integrity of the connective tissue.

As represented in FIG. 8, the delivery of energy from the electrodes 112A and 112B to an inflow of fluid media, such as any saline solution, will cause its instant vaporization and the expansion of the vapor will cause high pressure gradients to propagate the heated vapor from the port 126 across interface 144 to interact with endovascular media. The pressurized fluid media source 160 and pressure control subsystem 165 also can be adapted to create a pressure gradient, or enhance the pressure gradients caused by vapor expansion, to controllably eject the heated vapor from the working surface 104. As seen in FIG. 8, the vaporized media 180 can transfer heat, effectively by means of convective heat transfer, to the vessel walls. The vaporized media is at about 100° C. as it crosses the interface 144 and pushes blood distally while at the same time causing the desired thermal effects in the vessel wall.

As shown in FIG. 8, the collagen in the vessel walls will shrink and/or denature (along with other proteins) to thereby collapse the vessel. This means of applying thermal energy to vessel walls can controllably shrink, collapse and occlude the vessel lumen to terminate blood flow therethrough, and offers substantial advantages over alternative procedures. Vein stripping is a much more invasive treatment. Rf closure of varicose veins as known in the art uses Rf electrodes to contact the vessel walls to collapse and damage the walls means of causing ohmic heating in the vessel walls. Such Rf ohmic heating cause several undesirable effects, such as (i) creating high peak electrode temperatures (up to several hundred degrees C.) that can ohmic heating and damage in nerves extending along the vessel exterior, (ii) causing non-uniform thermal effects about valves making vessel closure incomplete, and (iii) causing vessel perforations in introducing the catheter-type instrument that is dragged along the vessel walls. In contrast, the energy delivery system of the invention utilizes heated vapor that cannot exceed 100° C. to apply energy to the vessel walls which is substantially prevents heat from being propagated heat outwardly by conduction—thus preventing damage to nerves. There is no possibility of causing ohmic heating in nerves, since a principal advantage of the invention is the application of therapeutic heat entirely without electrical current flow in tissue. Further, the vapor and its heat content can apply substantially uniform thermal effects about valves since the heat transfer mechanism is through a heated gas that contacts all vessel wall surfaces-and is not an electrode that is dragged along the vessel wall. Further, the vapor 180 can be propagated from the working end 100 while maintained in a single location, or a plurality of locations. Thus, the system of the invention may not require the navigation of the member 102 through tortuous vessels. Alternatively, the working end 100 may be translated along the lumen as energy is applied by means of convention.

Another advantage of the invention is that the system propagates a therapeutic vapor media from the working end surface 104 that can be imaged using conventional ultrasound imaging systems. This will provide an advantage over other heat transfer mechanisms, such as ohmic heating, that cannot be directly imaged with ultrasound.

The working end 100 and its method of use as depicted in FIGS. 7–8 can to apply therapeutic heat to blood vessel wall to treat chronic vascular insufficiency (CVI). In this disorder, venous valves are impaired or non-functional due in part to vessel swelling and distention proximate to the valves. The working end 100 as depicted in FIG. 8 can be positioned within the vessel to apply heat to the distended vessel wall portions to restore venous valve function. Intraoperative ultrasound can be used to image the procedure. The working end 100 and method can also be used to shrink AVMs (arterial vascular malformations) and aneurysms.

In another method of the invention, the working end 100 as depicted in FIGS. 7–8 can be used to apply therapeutic heat to any duct, cavity, lumen, septae or the like in the body to shrink, collapse or damage the anatomic walls or to fuse together and seal endothelial layers thereof. For example, the system and method can be used for tubal ligation in a treatment of fallopian tubes, or for closing microvasculature terminate blood flow to vascularized diseased tissue, tumors and the like. Such embolic, vessel closure methods are used to starve cancerous tissues and fibroids from blood flow. Such vessel closure methods are also can be used to starve blood flow from alveoli in a lung volume reduction procedure for treating emphysema. The working end 100 can also be introduced within the patient's airways to directly deliver therapeutic heat to airways to cause their collapse to cause lung volume reduction.

The above Type "B" systems and methods have been described for use in endoluminal environments wherein the propagation of heated matter (vapor) can function optimally (i) within a fluid in the lumen, (ii) by displacing the fluid in the lumen, or (iii) by expanding a space within a collapsed lumen, duct, septae or the like. It should be appreciated that the systems and methods of the invention also can be used to apply energy directly to the interior of soft tissue volumes, for example to kill tumors. The heat vapor will propagate within extracellular spaces to thereby cause therapeutic heating for any purpose.

The Type "B" system described above has opposing polarity electrodes to deliver energy to the inflowing fluid media. In an alternative embodiment (not shown), a resistive element can be used made out of any suitable material such as tungsten. The system can apply high levels of energy to the resistive element that interfaces with the inflowing fluid media. The superheated resistive element can vaporize the fluid media as describe above. The resistive element can be helical, tubular or a microporous structure that allows fluid flow therethrough.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A method for applying energy to endovascular media, comprising the steps of:
   (a) providing an apparatus comprising an electrical discharge source and a member having a working end surface with a longitudinal open-ended channel therein that carries first and second spaced apart interior electrodes, the first and second electrodes coupled to the electrical discharge source;
   (b) introducing the working end surface of the member to an endovascular location proximate the targeted media thereby defining an interface of the working end surface and the targeted media;
   (c) introducing a fluid having a specified electrical resistivity into the channel; and
   (d) establishing an intense electrical field across the fluid between the first and second electrodes causing vaporization of the fluid to deliver thermal energy across the interface to the targeted media.

2. The method of claim 1 wherein the vaporization creates a pressure gradient that projects the fluid vapor from the working end surface.

3. The method of claim 1 wherein step (c) introduced the fluid under a selected level of pressure which creates a pressure gradient that projects the fluid vapor from the working end surface.

4. The method of claim 1 wherein step (d) includes the step of causing thermal effects in the walls of the vasculature within the class of effects consisting of vessel wall shrinkage, vessel occlusion, endothelial layer damage and endothelial layer sealing.

5. The method of claim 1 wherein step (d) includes the step of causing vessel wall shrinkage to treat arterial vascular malformations.

6. The method of claim 1 wherein step (d) includes the step of causing vessel wall shrinkage to treat varicose veins.

7. The method of claim 1 wherein step (d) includes the step of causing an embolism to terminate blood flow to targeted tissues.

8. A medical instrument for application of energy to endoluminal body structure of a patient, comprising:
   an instrument having a proximal handle end and a working end dimensioned for endoluminal introduction, the working end defining an energy-delivery interface between a working end surface and targeted body structure;
   at least one bore in the working end terminating in a media entrance port in the working end surface, a proximal portion of the at least one bore fluidly coupled to a pressurized fluid media source, and a thermal energy emitter carried at an interior portion of the at least one bore for causing vaporization of the fluid media within the at least one bore to thereby cause high pressure gradients within the at least one bore to project heated vapor across the energy-delivery interface toward the targeted endoluminal body structure.

9. The instrument of claim 8 wherein the thermal energy emitter comprises at least one electrode coupled to an electrical source.

10. The instrument of claim 9 wherein the at least one electrode comprises spaced apart opposing polarity electrodes in an intertwined helical configuration.

11. The instrument of claim 8 wherein the thermal energy emitter comprises a resistive element coupled to an electrical source.

12. The instrument of claim 11 wherein the resistive element comprises a microporous body.

13. The instrument of claim 8 wherein the thermal energy emitter comprises the terminal end of a light channel coupled to a light source.

14. The instrument of claim 8 wherein the fluid media is a saline solution.

15. The instrument of claim 8 wherein the fluid media carries a chromophore.

16. A method for applying energy to body structure, comprising the steps of:
   providing an apparatus comprising a thermal energy emitter in an interior bore of an instrument that communicates with an open-ended channel in an instrument working end surface, the emitter coupled to a remote energy source and controller;
   introducing the working end surface of the apparatus into the interior of the body of a patient; introducing a fluid media having a specified heat capacity into the interior bore wherein the working end surface defines an interface between the apparatus and body structure; and
   delivering energy to the fluid media from the emitter to vaporize the fluid wherein heated vapor media is propagated across the interface to apply thermal energy to the body structure.

17. The method of claim 16 wherein the delivering step applies thermal energy to endoluminal media.

18. The method of claim 17 wherein the delivering step applies thermal energy to cause thermal effects in endoluminal structure within the class of effects consisting of luminal wall shrinkage, occlusion, damage, sealing and the creation of an embolism.

19. The method of claim 16 further comprising the step of imaging the vapor media propagated across the interface with ultrasound.

20. The method of claim 16 wherein the delivering step applies thermal energy to the interior of soft tissue.

* * * * *